United States Patent
Witt et al.

(10) Patent No.: US 8,556,951 B2
(45) Date of Patent: Oct. 15, 2013

(54) SYSTEM AND METHOD OF TITRATING A PHOTOTHERAPY REGIME USING REAL-TIME EEG READINGS

(75) Inventors: Erik Kurt Witt, Murrysville, PA (US); Mark Toddman Kirby, Spring Church, PA (US)

(73) Assignee: Koninklijke Philips N.V., Eindhoven (NL)

(*) Notice: Subject to any disclaimer, the term of this patent is extended or adjusted under 35 U.S.C. 154(b) by 0 days.

(21) Appl. No.: 13/318,544

(22) PCT Filed: May 11, 2010

(86) PCT No.: PCT/IB2010/052092
§ 371 (c)(1),
(2), (4) Date: Nov. 2, 2011

(87) PCT Pub. No.: WO2010/140073
PCT Pub. Date: Dec. 9, 2010

(65) Prior Publication Data
US 2012/0053395 A1    Mar. 1, 2012

Related U.S. Application Data

(60) Provisional application No. 61/183,800, filed on Jun. 3, 2009.

(51) Int. Cl.
*A61N 5/06*    (2006.01)

(52) U.S. Cl.
USPC .............................................. 607/88

(58) Field of Classification Search
None
See application file for complete search history.

(56) References Cited

U.S. PATENT DOCUMENTS

| | | | | |
|---|---|---|---|---|
| 4,858,609 | A * | 8/1989 | Cole | 607/91 |
| 5,495,853 | A * | 3/1996 | Yasushi | 600/545 |
| 5,507,716 | A * | 4/1996 | LaBerge et al. | 600/27 |
| 6,669,627 | B1 * | 12/2003 | Campbell et al. | 600/27 |
| 2005/0012622 | A1 * | 1/2005 | Sutton | 340/573.1 |
| 2005/0283039 | A1 * | 12/2005 | Cornel | 600/27 |
| 2006/0106275 | A1 * | 5/2006 | Raniere | 600/26 |
| 2006/0200011 | A1 * | 9/2006 | Suzuki et al. | 600/301 |
| 2006/0293608 | A1 * | 12/2006 | Rothman et al. | 600/545 |
| 2007/0083079 | A1 * | 4/2007 | Lee et al. | 600/27 |
| 2011/0257712 | A1 * | 10/2011 | Wells et al. | 607/90 |
| 2012/0209355 | A1 * | 8/2012 | Witt et al. | 607/88 |

* cited by examiner

*Primary Examiner* — Bill Thomson
*Assistant Examiner* — Lynsey Crandall
(74) *Attorney, Agent, or Firm* — Timothy A. Nathan

(57) ABSTRACT

The provision of phototherapy to a subject is titrated to adapt dynamically to the sleep of the subject. The titration is performed using real-time or near real-time EEG readings. This may enhance the comfort and/or efficacy of the phototherapy.

9 Claims, 3 Drawing Sheets

SYSTEM AND METHOD OF TITRATING A PHOTOTHERAPY REGIME USING REAL-TIME EEG READINGS

This application is related to U.S. Patent Application Ser. No. 61/141,273, entitled "SYSTEM AND METHOD FOR PROVIDING LIGHT THERAPY TO A SUBJECT," filed Dec. 30, 2008; and U.S. Patent Application Ser. No. 61/141,289, entitled "SYSTEM AND METHOD FOR ADMINISTERING LIGHT THERAPY," filed Dec. 30, 2008. Both of these applications are hereby incorporated into this application in their entirety.

The invention relates to the titration of phototherapy provided by a consumer phototherapy sleep mask using real-time EEG readings.

The direction of radiation on a subject to impact the Circadian rhythms and/or to address disorders of the subject related to melatonin and/or serotonin levels in the subject are known. Generally, these treatments involve shining light directly towards a patient's eyes while the patient is awake to alleviate or cure light deficient disorders including Seasonal Affective Disorder (SAD), circadian sleep disorders and circadian disruptions associated with jet-lag, and shift-work.

While some systems may be configured to administer phototherapy to a subject as the subject sleeps, these systems tend to implement static phototherapy regimes that are not dynamically adaptive to the sleep of the subject.

One aspect of the invention relates to a system configured to provide light therapy to a subject as the subject sleeps. In one embodiment, the system comprises a sleep mask and a processor. The sleep mask comprises a shield, a headgear, one or more lighting modules, and one or more EEG electrodes. The shield is configured to cover the eyes of a subject wearing the sleep mask such that the shield provides a barrier between ambient radiation and the eyes of the subject. The headgear is configured to hold the shield in place on the face of the subject. The one or more lighting modules are carried by the shield, and are configured to provide radiation to the eyes of the subject. The one or more EEG electrodes are carried by the shield and/or the headgear. The processor is in operative communication with the one or more lighting modules and the one or more EEG electrodes, and is configured (i) to control the one or more lighting modules to emit radiation incident on the eyes of the subject to provide phototherapy to the subject, (ii) to receive output signals generated by the one or more EEG electrodes, and (iii) to adjust one or more parameters of the phototherapy provided to the subject based on the received output signals.

Another aspect of the invention relates to a method of providing light therapy to a subject as the subject sleeps. In one embodiment, the method comprises covering the eyes of a subject with a shield such that the shield provides a barrier between ambient radiation and the eyes of the subject; holding the shield in place on the face of the subject with a headgear; receiving output signals generated by one or more EEG electrodes carried by one or both of the shield and/or the headgear; and controlling one or more lighting modules carried by the shield to emit radiation incident on the eyes of the subject to provide phototherapy to the subject, wherein one or more parameters of the phototherapy provided to the subject are based on the received output signals.

Another aspect of the invention relates to a system configured to provide light therapy to a subject as the subject sleeps. In one embodiment, the system comprises means for covering the eyes of a subject that a barrier between ambient radiation and the eyes of the subject; means for holding the means for covering the eyes in place on the face of the subject; means for receiving output signals generated by one or more EEG electrodes carried by one or both of the means for covering the eyes and/or the means for holding; and means for controlling one or more lighting modules carried by the means for covering the eyes to emit radiation incident on the eyes of the subject to provide phototherapy to the subject, wherein one or more parameters of the phototherapy provided to the subject are based on the received output signals.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
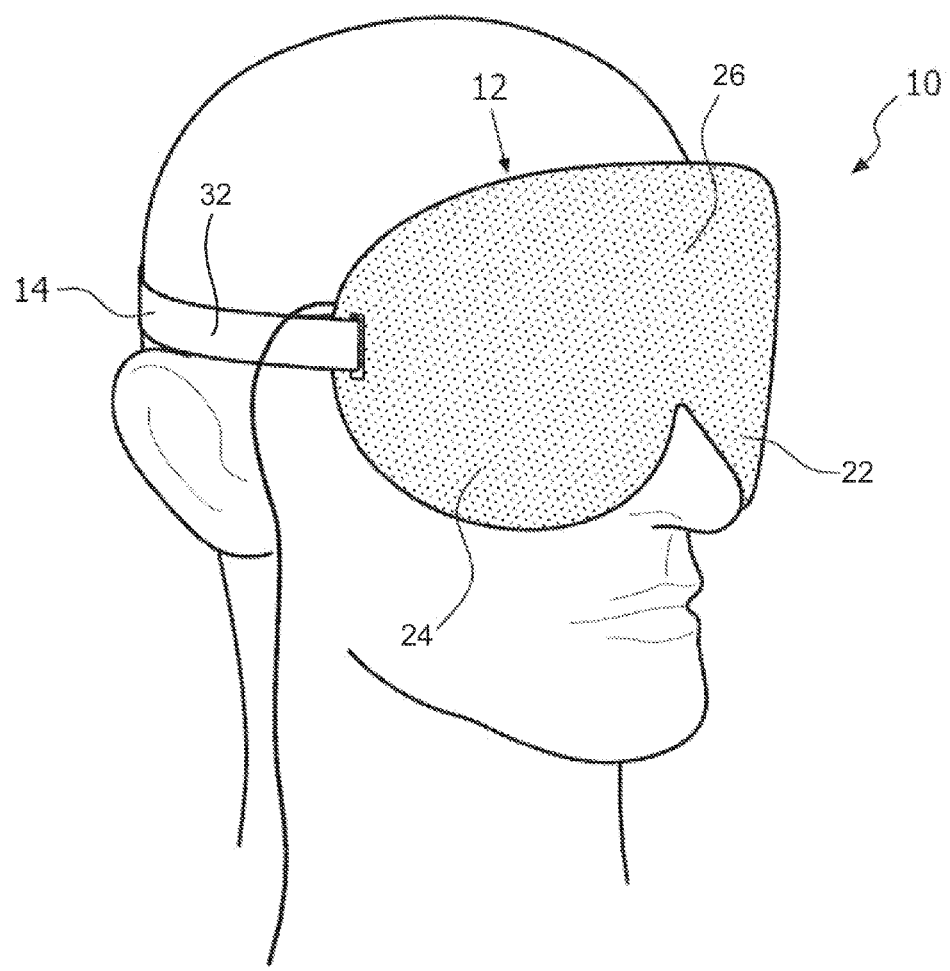
FIG. 1 illustrates a sleep mask configured to provide light therapy to a subject, in accordance with one or more embodiments of the invention.
Figure 2:
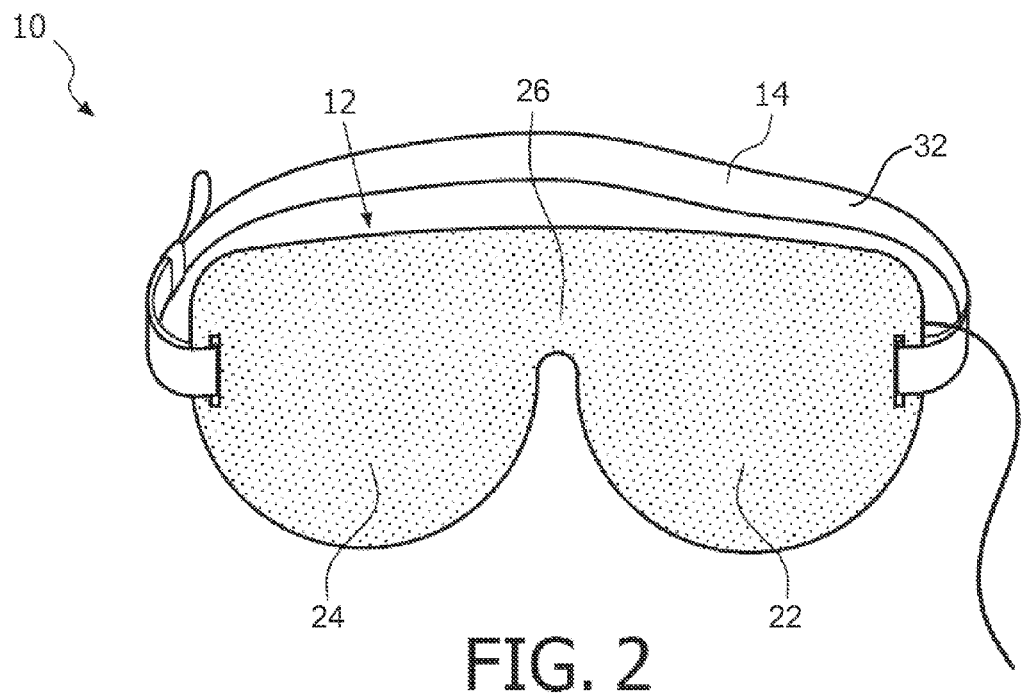
FIG. 2 illustrates a sleep mask configured to provide light therapy to a subject, in accordance with one or more embodiments of the invention.
Figure 3:
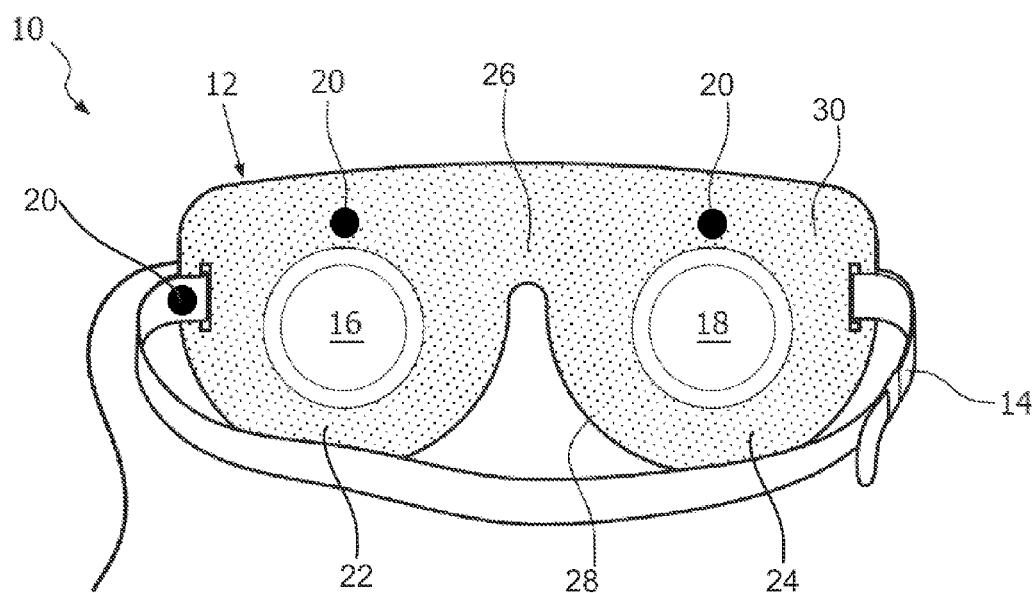
FIG. 3 illustrates a sleep mask configured to provide light therapy to a subject, in accordance with one or more embodiments of the invention.

FIGS. 1-3 illustrate a sleep mask 10 configured to provide light therapy to a subject. Sleep mask 10 may provide a comfortable delivery mechanism for the light therapy, and may deliver the light therapy to the subject while the subject is asleep, in the process of going to sleep, and/or waking from sleep. In one embodiment, sleep mask 10 includes one or more of a shield 12, a headgear 14, a first lighting module 16, a second lighting module 18, and/or one or more electrodes 20.

As can be seen in FIG. 1, shield 12 is configured to cover the eyes of the subject wearing sleep mask 10. In one embodiment, shield 12 includes a first shield portion 22 and a second shield portion 24. First shield portion 22 is configured to cover a first eye of the subject. Second shield portion 24 is configured to cover a second eye of the subject. In order to comfortably cover the first eye and the second eye of the subject, first shield portion 22 and second shield portion 24 are substantially larger than the ocular openings of the eyes of the subject.

In one embodiment, first shield portion 22 and second shield portion 24 are joined by a connecting shield portion 26. Connecting shield portion 26 is configured to rest on at least a portion of the nose of the subject (e.g., across the bridge of the nose) when the subject is wearing sleep mask 10. In some instances (not shown), connecting shield portion 26 may be narrower or thicker than the embodiment depicted in FIGS. 1-3.

In one embodiment, shield 12 is formed from flexible materials. The flexibility of shield 12 may enhance the comfort of shield 12 to the subject. The side of shield 12 visible in FIG. 3 faces toward the subject during use. On this side, a base surface 28 substantially impermeable to liquids may be formed. For example, the impermeable base surface 28 may be formed by a flexible plastic material such as polycarbonate, polyester, and/or other materials. The impermeability of base surface 28 may protect electronic components of sleep mask 10 carried within shield 12 from moisture.

In one embodiment, shield 12 includes a cushioning layer 30 disposed on base surface 28. Cushioning layer 30 is formed from a soft, resilient material. For example, cushioning layer 30 may be formed from foam, foam, fabric/foam laminate, and/or other materials. During use, cushioning layer 30 provides the innermost surface to the subject, and engages the face of the subject. As such, the softness of cushioning layer 30 provides a cushion for the face of the subject, and enhances the comfort of sleep mask 10 to the subject.

As will be appreciated from the foregoing and FIGS. 1-3, during use shield 12 provides a barrier between ambient radiation and the eyes of the subject. In one embodiment, shield 12 is opaque, and blocks ambient radiation (at least within the visible spectrum), thereby shielding the eyes of the subject from ambient radiation.

Headgear 14 is configured to hold shield 12 in place on the subject. In the embodiments shown in FIGS. 1-3, headgear 14 includes a strap 32 attached to each of first shield portion 22 and second shield portion 24. The strap 32 wraps around the head of the subject to hold sleep mask 10 in place on the head of the subject. Strap 32 may be adjustable in length (e.g., to accommodate different sized heads). Strap 32 may be formed from a resilient material (e.g., elastic) that stretches to accommodate the head of the user and holds shield 12 in place. It should be appreciated that the inclusion of strap 32 in the embodiments of sleep mask 10 illustrated in FIGS. 1-3 is not intended to be limiting. Other mechanisms for holding shield 12 in place on the subject are contemplated as headgear 14. For example, a more elaborate set of straps may be implemented, an adhesive surface may be applied to shield 12 that removably adheres to the skin of the subject to hold shield 12 in place, and/or other mechanisms for holding shield 12 in place may be implemented as headgear 14.

Referring now to FIG. 3, first lighting module 16 and second lighting module 18 are mounted to first shield portion 22 and second shield portion 24, respectively, on the side of shield 12 that faces toward the face of the subject during use. First lighting module 16 and second lighting module 18 are backlit, and are configured to emit radiation onto the face of the subject on and/or about the eyes of the subject. The radiation emitted by first lighting module 16 and second lighting module 18 has a wavelength (or wavelengths) that have a therapeutic impact on the subject, when they are delivered in accordance with an effective phototherapy regime (e.g., 410 nm-580 nm, blue-green, around 480 nm, etc.).

The electrodes 20 are carried by sleep mask 10 on shield 12 and/or headgear 14. By way of non-limiting example, in the embodiment illustrated in FIG. 3, electrodes 20 include two electrodes 20 carried by shield 12 and one electrode 20 carried by strap 32. The electrodes 20 carried by shield 12 are disposed on shield 12 so as to be positioned over the ocular cavities (e.g., on the brow) of a subject when sleep mask 10 is mounted for use on the head of the subject. The electrode 20 carried by strap 32 is disposed on strap 32 such that electrode 20 is positioned behind the ear of the subject when sleep mask 10 is mounted for use on the head of the subject.

In the embodiment illustrated in FIG. 3, electrodes 20 are mounted directly to shield 12 and strap 32. This is not intended to be limiting. In some embodiments, one or more of electrodes 20 may be connected to sleep mask 10 by a short lead. This may enable the subject to individually position an electrode on his face without re-positioning the entire sleep mask 10. However, this type of configuration may increase the time it takes to install sleep mask 10 on the head for use, as the electrodes 20 connected to sleep mask 10 by a short lead may have to be individually positioned.

The electrodes 20 may be formed as flat conductors that are placed in contact with the skin of the subject so as to pick up electrical activity caused by the firing of neurons in the brain. One or more of electrode 20 may include a mechanism for releasably adhering to the skin of the subject. For example, an adhesive coating may be applied to the surface of electrode 20, electrode 20 may be shaped to adhere to the skin of the subject via suction, and/or other mechanisms may be implemented to adhere the surface of electrode 20 to the skin of the subject to ensure that electrical activity produced by the brain are picked up by electrode 20.

The electrodes 20 illustrated in FIG. 3 are disposed on sleep mask 10 in positions that are likely to contact areas on the head of the subject that are not covered with hair. Hair positioned between electrodes 20 and the skin of the subject may disrupt the reception of electrical activity by electrodes 20.

In one embodiment, one or more of electrodes 20 are formed by cushioning layer 30. For example, some or all of cushioning layer 30 may be formed from a conductive foam material that serves as one or more electrodes 20 in receiving electrical signal generated by the brain of the subject.

In one embodiment, electrodes 20 include one or more electrooculograpy (EOG) electrodes (not shown) disposed on first shield portion 22 and/or second shield portion 24. In this embodiment, the EOG electrodes may be positioned around the portions of first shield portion 22 and/or second shield portion 24 contact the eyes of the subject. The EOG electrodes generate output signals that convey information about the rotational position of the eyeballs of the subject in the eyesockets.

Figure 4:
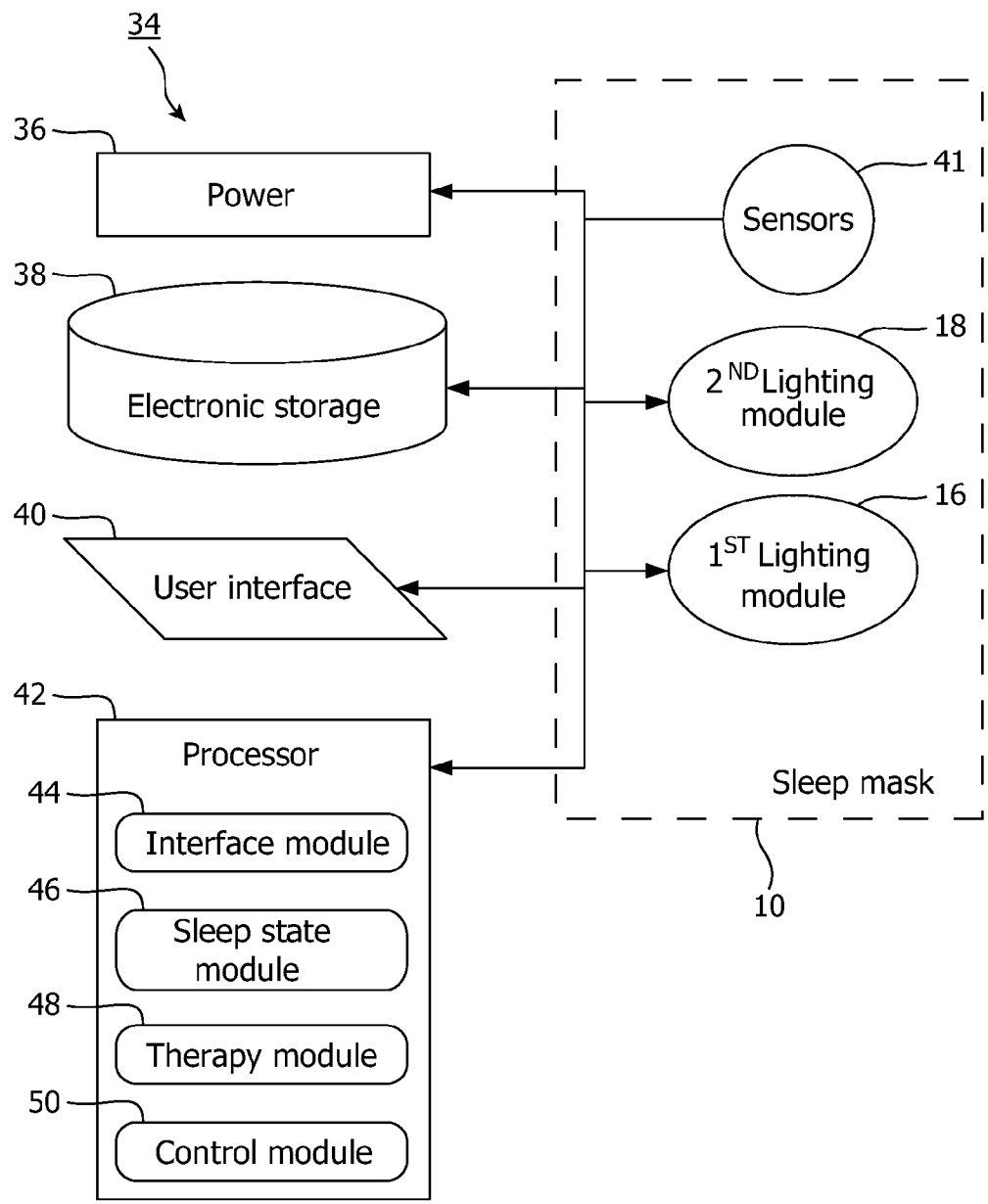
FIG. 4 illustrates a system configured to provide light therapy to a subject, in accordance with one or more embodiments of the invention.

FIG. 4 is a schematic illustration of a system 34 that includes sleep mask 10, in accordance with one or more embodiments of the invention. As can be seen in FIG. 4, in addition to one or more of the components shown in FIGS. 1-3 and described above, system 34 may include sleep mask 10, a power source 36, electronic storage 38, a user interface 40, one or more sensors 41, and/or a processor 42. In one embodiment, one or more of power source 36, electronic storage 38, user interface 40, one or more electrodes 20, and/or processor 42 are carried on shield 12 and/or strap 14 of sleep mask 10. In this embodiment, one or more of power source 36, electronic storage 38, user interface 40, one or more sensors 41, and/or processor 42 may be removably attached to shield 12 and/or headgear 14, and may be disconnectable from the rest of sleep mask 10. This will enable power source 36, electronic storage 38, user interface 40, one or more sensors 41 and/or processor 42 to be removed from a given shield 12 and/or headgear 14, and attached to another shield 12 and/or headgear 14. This may be beneficial if shield 12 and/or headgear 14 degrade over time and/or with usage and must be replaced. Similarly, in one embodiment, first lighting module 16 and second lighting module 18 are also removable/replaceable on shield 12. Power source 36, electronic storage 38, user interface 40, one or more sensors 41 and/or processor 42 may control operation the radiation sources associated with first lighting module 16 and/or second lighting module 18, as is discussed below.

Power source 36 provides the power necessary to operation the radiation sources associated with first lighting module 16 and second lighting module 18, and/or to power electronic storage 38, user interface 40, and/or processor 42. Power source 36 may include a portable source of power (e.g., a battery, a fuel cell, etc.), and/or a non-portable source of power (e.g., a wall socket, a large generator, etc.). In one embodiment, power source 36 includes a portable power source that is rechargeable. In one embodiment, power source 36 includes both a portable and non-portable source of power, and the subject is able to select which source of power should be used to provide power to sleep mask 10.

In one embodiment, electronic storage 38 comprises electronic storage media that electronically stores information. The electronically storage media of electronic storage 38 may include one or both of system storage that is provided integrally (i.e., substantially non-removable) with system 34 and/or removable storage that is removably connectable to system 34 via, for example, a port (e.g., a USB port, a firewire port, etc.) or a drive (e.g., a disk drive, etc.). Electronic storage 38 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 38 may store software algorithms, information determined by processor 42, information received via user interface 40, and/or other information that enables system 34 to function properly. Electronic storage 38 may include media provided as a separate component within sleep mask 10. Electronic storage 38 may include media provided integrally with one or more other components of system 34 (e.g., processor 42).

User interface 40 is configured to provide an interface between system 34 and the subject (and/or a caregiver) through which the subject (and/or a caregiver) may provide information to and receive information from system 34. This enables data, results, and/or instructions and any other communicable items, collectively referred to as "information," to be communicated between the subject and processor 42. Examples of interface devices suitable for inclusion in user interface 40 include a keypad, buttons, switches, a keyboard, knobs, levers, a display screen, a touch screen, speakers, a microphone, an indicator light, an audible alarm, and a printer. In one embodiment, the functionality of which is discussed further below, user interface 40 actually includes a plurality of separate interfaces, including one interface that is carried on system 34, and a separate interface provided to view and/or manage stored information that has been retrieved from system 34 (e.g., provided by a host computer to which information from system 34 can be received).

It is to be understood that other communication techniques, either hard-wired or wireless, are also contemplated by the present invention as user interface 40. For example, the present invention contemplates that user interface 40 may be integrated with a removable storage interface provided by electronic storage 38. In this example, information may be loaded into system 34 from removable storage (e.g., a smart card, a flash drive, a removable disk, etc.) that enables the user(s) to customize the implementation of system 34. Other exemplary input devices and techniques adapted for use with system 34 as user interface 40 include, but are not limited to, an RS-232 port, RF link, an IR link, modem (telephone, cable or other). In short, any technique for communicating information with system 34 is contemplated by the present invention as user interface 40.

Sensors 41 generate output signals that convey information about one or more physiological parameters of a subject that are indicative of the sleep-state of the subject. The sleep-state of the subject may refer to a sleep stage of the sleep of the subject, a sleepiness of the subject, a wakefulness of the subject and/or other information related to the sleep-state of the subject. As an example, sensors 41 may include one or more of EEG and/or EOG electrodes 20 (shown in FIG. 3 and discussed above), a pulse oximeter, a photoplethysmographic sensor, an electrocardiographic electrode, a pulse rate sensor, sensors configured to detect eyeball and/or eyelid motion (e.g., as described in the U.S. patent application entitled "SYSTEM AND METHOD FOR ADMINISTERING LIGHT THERAPY," and incorporated by reference into this disclosure above), and/or other sensors. In one embodiment, a transmissive pulse oximeter sensor is included in sensors 41, and is configured to attach to an ear of the subject. The transmissive pulse oximeter may be attached to a headgear associated with mask 10 (e.g., headgear 14 shown in FIGS. 1-3 and described above), and/or connected to the headgear via an electrical lead. The transmissive pulse oximeter may be configured to generate output signals that enable generation of a photoplethysmograph. The output signals generated by sensors 41 are conveyed to processor 42 by an operative link with processor 42. The operative link may include a wired and/or wireless connection.

Processor 42 is configured to provide information processing capabilities in system 34. As such, processor 42 may include one or more of a digital processor, an analog processor, a digital circuit designed to process information, an analog circuit designed to process information, a state machine, and/or other mechanisms for electronically processing information. Although processor 42 is shown in FIG. 1 as a single entity, this is for illustrative purposes only. In some implementations, processor 42 may include a plurality of processing units. These processing units may be physically located within the same device, or processor 40 may represent processing functionality of a plurality of devices operating in coordination. For example, in one embodiment, the functionality attributed below to processor 40 is divided between a first processor that is by sleep mask 10, and a second processor that communicates with sleep mask 10 at least periodically to obtain information generated by electrodes 20 and/or the first processor.

As is shown in FIG. 4, processor 42 is configured to execute one or more computer program modules. The one or more computer program modules may include one or more of an interface module 44, a sleep state module 46, a therapy module 48, a control module 50, and/or other modules. Processor 42 may be configured to execute modules 44, 46, 48, and/or 50 by software; hardware; firmware; some combination of software, hardware, and/or firmware; and/or other mechanisms for configuring processing capabilities on processor 42.

It should be appreciated that although modules 44, 46, 48, and/or 50 are illustrated in FIG. 4 as being co-located within a single processing unit, in implementations in which processor 42 includes multiple processing units, one or more of modules 44, 46, 48, and/or 50 may be located remotely from the other modules. The description of the functionality provided by the different modules 44, 46, 48, and/or 50 described below is for illustrative purposes, and is not intended to be limiting, as any of modules 44, 46, 48, and/or 50 may provide more or less functionality than is described. For example, one or more of modules 44, 46, 48, and/or 50 may be eliminated, and some or all of its functionality may be provided by other ones of modules 44, 46, 48, and/or 50. As another example, processor 42 may be configured to execute one or more additional modules that may perform some or all of the functionality attributed below to one of modules 44, 46, 48, and/or 50.

Interface module 44 is configured to enable communication between system 34 and a user (e.g., the subject, a caregiver, etc.) via user interface 40. To enable such communication, interface module 44 receives information input to system 34 via user interface 40 and interprets and/or formats the received information such that other components of system 34 can implement the inputs. Further, interface module 44 may generate output information for transmission to user interface 40 that is output to the user via user interface 40.

The sleep state module 46 is configured to determine information related to the sleep state of the subject. The sleep state module 46 determines this information at least in part from the output signals of sensors 41. As was mentioned above, the output signals generated by sensors 41 convey information related to one or more physiological parameters of the subject. The one or more physiological parameters may include one or more of electrical signals generated by brain activity of the subject, arterial hemoglobin in the oxyhemoglobin configuration, blood volume in the skin, eyeball and/or eyelid motion and/or position, pulse rate, pulse rate variability, electrical activity of the heart, and/or other physiological parameters. The information is determined by sleep state module 46 in real-time (or near real-time). The information determined by sleep state module 46 may include, for example, whether the subject is in REM sleep or non-REM sleep, a current sleep stage (e.g., stage 1 sleep, stage 2 sleep, or stage 3 sleep), information related to the Circadian rhythm of the subject (e.g., current Circadian phase, and/or other information), and/or other information related to the sleep state of the subject.

The therapy module 48 is configured to manage the phototherapy regime administered to the subject by system 34. In particular, therapy module 48 manages a phototherapy regime that impacts the cones, rods, and/or photoresponsive retinal ganglion cells of the eyes, retinohypothalamic tract, suprachiasmatic nucleus (or nuclei) in the hypothalamus, pineal gland, and the secretion of the hormone melatonin. Other structures and functions of the brain involved in the circadian rhythm and mood, as well as other hormones (e.g., serotonin) that are impacted by phototherapy are not detailed here, but are known in the art. Managing the phototherapy regime administered to the subject by system 34 may include accessing, configuring, and/or determining one or more parameters of the phototherapy regime. The one or more parameters of the phototherapy regime may include a start time of a therapy session, an end time of a therapy session, a duration of a therapy session, one or more parameters of the electromagnetic radiation provided to the eyes of the subject during a session, breathing patterns, and/or other parameters. The one or more parameters of the electromagnetic radiation provided to the eyes of the subject during a session may include one or more of an intensity, a luminance, a wavelength, a flux, a timing, a duration, a pulse frequency, a pulse width, an illumination direction, an illumination pattern, a subtended angle of illumination, and/or other parameters.

In one embodiment, therapy module 48 enables the user to select a specific phototherapy regime, and/or individual parameters of a phototherapy regime. The user may enter selections of phototherapy regimes and/or parameters of a phototherapy regime via user interface 40.

The control module 50 is configured to control first lighting module 16 and second lighting module 18 in accordance with the phototherapy regime. This includes operating the lighting modules 16 and 18 to provide therapy sessions according to the parameters of the phototherapy regime determined by therapy module 48.

In one embodiment, the determination of the phototherapy regime by therapy module 48, and the execution of the phototherapy regime by control module 50 is adaptive and dynamic. This includes adjusting parameters of the phototherapy regime in real-time (or near real-time) on the sleep state of the subject determined by sleep state module 46.

By way of non-limiting example, in one embodiment, the phototherapy regime is determined by therapy module 48 to treat Phase Delay Syndrome in the subject. "Night-owl" teenagers commonly suffer from a late-night shifted sleeping schedule associated with Phase Delay Syndrome. To treat Phase Delay Syndrome, the phototherapy regime determined by therapy module 48 dictates that efficacious levels of electromagnetic radiation should be delivered to the subject after the subject's Circadian phase-zero towards the morning. This administration of electromagnetic radiation via system 34 may be coupled with restricted light exposure and exogenous melatonin administration prior to bed time. Such treatment is known as Phase Advance treatment regime.

In order to more effectively administer the electromagnetic radiation during a Phase Advance treatment regime, sleep state module 46 may identify the Circadian phase-zero of the subject. Based on this identification, therapy module 48 then adjusts the timing of the Phase Advance treatment regime. This may include triggering control module 50 to commence administration of electromagnetic radiation to the subject at the identified Circadian phase-zero.

As another example, of how therapy module 48 may adjust a parameter of a phototherapy regime based on the sleep state of the subject, therapy module 48 may adjust one or more parameters of the phototherapy regime to reduce and/or account for arousals of the subject.

For instance, during sleep the administration of electromagnetic radiation to the subject by lighting modules 16 and 18 may tend to arouse the subject. If sleep state module 46 detects a progression in the sleep state of the subject that indicates that the subject may be in the process of waking, therapy module 48 may adjust one or more parameters of the phototherapy being administered (e.g., an intensity of the electromagnetic radiation, and/or other parameters) that could contribute to the wakefulness of the subject. More specifically, in a non-limiting example, if sleep state module 46 determines that the subject has moved from non-REM sleep to REM sleep, therapy module 48 may adjust the parameters of the phototherapy regime such that control module 50 causes lighting modules 16 and 18 to reduce the intensity of the electromagnetic radiation provided to the eyes of the subject. This may reduce the arousals caused by the phototherapy regime. Further, this type of adjustment may reduce discomfort to the subject if the subject opens his eyes as he awakens (e.g., since the intensity will have been reduced).

Similarly, the determination of sleep state by sleep state module 46 to progressively adjust one or more parameters of the phototherapy regime (e.g., intensity, and/or other parameters) as the subject goes to sleep. For instance, as sleep state module 46 determines that the subject has fallen asleep (after an arousal or upon going to bed), therapy module 48 may cause control module 50 to begin the administration of electromagnetic radiation at a reduced intensity level. Then, as sleep state module 46 determines that the sleep of the subject is becoming deeper, therapy module 48 may cause control module 50 to increase the intensity of the electromagnetic radiation delivered by lighting modules 16 and 18 to the eyes of the subject.

As another example of the manner in which therapy module 48 may dynamically and adaptively adjust one or more parameters of the phototherapy regime, therapy module 48 may adjust the phototherapy regime to account for therapy time "lost" during arousals or partial arousals. This could include increasing the duration, luminance, flux, intensity, and/or other parameter of the phototherapy regime to make up for time during which the administration of electromagnetic radiation to the subject as part of the phototherapy regime was reduced or suspended in accordance with determinations related to sleep state by sleep state module 46.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system configured to provide light therapy to a subject as the subject sleeps, the system comprising:
   a sleep mask, the sleep mask comprising:
      a shield configured to cover the eyes of a subject wearing the sleep mask such that the shield provides a barrier between ambient radiation and the eyes of the subject;
      a headgear configured to hold the shield in place on the face of the subject;
      one or more lighting modules carried by the shield, the one or more lighting modules being configured to provide radiation to the eyes of the subject; and
      one or more EEG electrodes carried by the shield and/or the headgear; and
   a processor in operative communication with the one or more lighting modules and the one or more EEG electrodes, the processor (i) controlling the one or more lighting modules to emit radiation incident on the eyes of the subject to provide phototherapy to the subject, (ii) receiving output signals generated by the one or more EEG electrodes, and (iii) adjusting one or more parameters of the phototherapy provided to the subject based on the received output signals
      wherein, the processor is configured such that adjusting one or more parameters of the phototherapy provided to the subject based on the received output signals comprises controlling the one or more lighting modules to emit radiation onto the eyes of the subject at a first intensity if the received output signals indicate that the subject is experiencing REM sleep, and at a second intensity if the received output signals indicate that the subject is experiencing non-REM sleep, and wherein the first intensity is less than the second intensity.

2. The system of claim 1, wherein the one or more parameters of the phototherapy provided to the subject that the processor is configured to adjust based on the received output signals comprise one or more of an intensity of the radiation emitted by the one or more lighting modules, a start time of the phototherapy, an end time of the phototherapy, or a duration of the phototherapy.

3. The system of claim 1, wherein the processor is carried by the sleep mask.

4. A method of providing light therapy to a subject as the subject sleeps, the method comprising:
   covering the eyes of a subject with a shield such that the shield provides a barrier between ambient radiation and the eyes of the subject;
   holding the shield in place on the face of the subject with a headgear;
   receiving output signals generated by one or more EEG electrodes carried by one or both of the shield and/or the headgear; and
   controlling one or more lighting modules carried by the shield to emit radiation incident on the eyes of the subject to provide phototherapy to the subject,
      wherein one or more parameters of the phototherapy provided to the subject are based on the received output signals and
      wherein controlling one or more lighting modules carried by the shield to emit radiation incident on the eyes of the subject to provide phototherapy to the subject comprises controlling the one or more lighting modules to emit radiation onto the eyes of the subject at a first intensity if the received output signals indicate that the subject is experiencing REM sleep, and at a second intensity if the received output signals indicate that the subject is experiencing non-REM sleep, and wherein the first intensity is less than the second intensity.

5. The method of claim 4, wherein the one or more parameters of the phototherapy provided to the subject that are based on the received output signals comprise one or more of an intensity of the radiation emitted by the one or more lighting modules, a start time of the phototherapy, an end time of the phototherapy, or a duration of the phototherapy.

6. The method of claim 4, wherein the reception of the output signals and the controlling of the one or more lighting modules are performed by a processor that is carried by the shield and/or the headgear.

7. A system configured to provide light therapy to a subject as the subject sleeps, the system comprising:
   means for covering the eyes of a subject that a barrier between ambient radiation and the eyes of the subject;
   means for holding the means for covering the eyes in place on the face of the subject;
   means for receiving output signals generated by one or more EEG electrodes carried by one or both of the means for covering the eyes and/or the means for holding; and
   means for controlling one or more lighting modules carried by the means for covering the eyes to emit radiation incident on the eyes of the subject to provide phototherapy to the subject,
      wherein one or more parameters of the phototherapy provided to the subject are based on the received output signals, and
      wherein controlling the one or more lighting modules comprises controlling the one or more lighting modules to emit radiation onto the eyes of the subject at a first intensity if the received output signals indicate that the subject is experiencing REM sleep, and at a second intensity if the received output signals indicate that the subject is experiencing non-REM sleep, and wherein the first intensity is less than the second intensity.

8. The system of claim 7, wherein the one or more parameters of the phototherapy provided to the subject that are based on the received output signals comprise one or more of an intensity of the radiation emitted by the one or more lighting modules, a start time of the phototherapy, an end time of the phototherapy, or a duration of the phototherapy.

9. The system of claim 7, wherein the means for receiving output signals and the means for controlling one or more lighting modules are carried by the means for covering the eyes and/or the means for holding.

* * * * *